US00PP17689P2

(12) United States Plant Patent
Hofmann

(10) Patent No.: US PP17,689 P2
(45) Date of Patent: May 1, 2007

(54) **NEW GUINEA *IMPATIENS* PLANT NAMED 'FISNICS THYST'**

(50) Latin Name: *Impatiens hawkeri*
Varietal Denomination: Fisnics Thyst

(75) Inventor: Birgit Christa Hofmann, Bendorf (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 11/330,446

(22) Filed: Jan. 12, 2006

(51) Int. Cl.
*A01H 5/00* (2006.01)

(52) U.S. Cl. ..... Plt./318

(58) Field of Classification Search ..... Plt./318
See application file for complete search history.

*Primary Examiner*—Anne Marie Grunberg
*Assistant Examiner*—Georgia Helmer
(74) *Attorney, Agent, or Firm*—Jondle & Associates P.C.

(57) ABSTRACT

A new New Guinea *Impatiens* plant particularly distinguished by large, round, almost flat, lavender flowers that are well above the foliage, an early to medium flowering response, medium green foliage with large leaves, and a medium sized plant habit that is round and bushy, is disclosed.

1 Drawing Sheet

Genus and species: *Impatiens hawkeri* W. Bull.
Variety denomination: 'Fisnics Thyst'.

BACKGROUND OF THE NEW PLANT

The present invention comprises a new and distinct cultivar of New Guinea *Impatiens,* botanically known as *Impatiens hawkeri* W. Bull, and hereinafter referred to by the cultivar name 'Fisnics Thyst'. The new cultivar originated from a hybridization made in the year 2001 in Hillscheid, Germany. The female parent was the proprietary New Guinea *Impatiens* plant 'K01-8180-1' (unpatented), while the male parent was the proprietary New Guinea *Impatiens* plant 'K01-8753-17' (unpatented). The seeds produced by the hybridization were sown in Galdar, Gran Canaria, Spain in the late Fall of 2001. A single plant selection was chosen for further evaluation and for asexual propagation in April 2002 in Galdar, Gran Canaria, Spain.

The new cultivar was created in 2001 in Hillscheid, Germany and has been asexually reproduced repeatedly by vegetative cuttings and tissue culture in Galdar, Gran Canaria, Spain and Hillscheid, Germany over a two-year period. 'Fisnics Thyst' has not been observed under all possible environmental conditions. The present invention has been found to retain its distinctive characteristics through successive asexual propagations.

Plant Breeder's Rights for this cultivar were applied for in Switzerland on Apr. 28, 2005 and in Canada on Apr. 20, 2005.

SUMMARY OF THE INVENTION

The following are the most outstanding and distinguishing characteristics of this new cultivar when grown under normal horticultural practices in Hillscheid, Germany and in Langley, British Columbia, Canada.

1. Lavender flower color;
2. Large, round, almost flat flowers well above the foliage;
3. Uniform, medium green foliage with large leaves;

4. A medium sized, round and bushy plant habit; and
5. An early to medium flowering response.

DESCRIPTION OF PHOTOGRAPH

This new New Guinea *Impatiens* plant is illustrated by the accompanying photograph which shows overall plant habit including blooms, buds, and foliage of the plant; the colors shown are as true as can be reasonably obtained by conventional photographic procedures. The photograph is of a whole plant about 13-to 14-weeks old, grown in a greenhouse in Hillscheid, Germany, in late Spring.

DESCRIPTION OF THE NEW CULTIVAR

The following detailed descriptions set forth the distinctive characteristics of 'Fisnics Thyst'. The data which define these characteristics were collected from asexual reproductions carried out in Hillscheid, Germany. The plant history was taken on 12-week old plants which were planted as rooted cuttings in 12-cm pots in late February 2004, and then grown in a greenhouse at a minimum temperature of 16° C. Color readings were taken under natural light in the greenhouse. Color references are primarily to The R.H.S. Colour Chart of The Royal Horticultural Society of London (R.H.S.) (2001).

DETAILED BOTANICAL DESCRIPTION OF THE NEW PLANT

Classification:
*Family.*—Balsaminaceae.
*Botanical.*—*Impatiens hawkeri* W. Bull.
*Common name.*—New Guinea *Impatiens.*

Parentage:
*Female parent.*—'K01-8180-1' a proprietary purple flowered New Guinea *Impatiens* plant (unpatented).
*Male parent.*—'K01-8753-17' a proprietary purple to violet flowered New Guinea *Impatiens* plant (unpatented).

Growth:

*Growth and branching habit.*—Medium to large size, round, bushy, and well-branched; the growth is indeterminate, though weak after the beginning of flowering.

*Height.*—14.8 cm.

*Width.*—30.5 cm.

*Propagation.*—Terminal tips for cuttings.

*Time to produce a finished flowering plant.*—9 to 10 weeks for a 12-cm pot.

*Time to initiate and develop roots.*—18 days at 22° C.

Branches:

*Average number.*—10 to 11.

*Length of branches.*—11 cm to 13 cm.

*Internode length.*—3.0 cm to 5.0 cm.

*Diameter of branches.*—0.7 cm to 0.9 cm.

*Stem color.*—RHS 185A (purple-brown); RHS 187C at tips.

Leaves:

*Arrangement.*—Primarily in whorls.

*Size.*—Length: 13.4 cm. Width: 4.8 cm.

*Shape.*—Elliptic.

*Margin.*—Slightly serrate, ciliated.

*Apex.*—Acuminate.

*Base.*—Acute.

*Color* (*mature leaves*).—Upper surface: RHS 137A (intense medium-green). Lower surface: RHS 138B (light-green).

*Color* (*immature leaves*).—Upper surface: near RHS 137D. Lower surface: RHS 138B (light-green).

*Texture.*—Somewhat glossy, glabrous, smooth or faintly rippled.

*Venation color.*—Upper surface: RHS 53D (pink) at the base of the leaf. Lower surface: RHS 53B (reddish).

*Variegation.*—None.

*Petioles.*—Length: 1.8 cm. Diameter: 0.3 cm to 0.4 cm. Color: Upper surface: RHS 53C (deep pink to red). Lower surface: RHS 53B (deep pink to red). Texture: Glabrous.

Flower buds:

*Shape.*—Ovoid.

*Size.*—Length: 2.7 cm. Diameter: 1.8 cm.

*Color.*—RHS N74B (light purple).

Inflorescence:

*Blooming habit.*—9 to 10 weeks after planting of rooted cuttings.

*Inflorescence type.*—Flowers appear solitary in the leaf axils of the upper nodes of the stems.

*Number of flowers per node.*—6 to 8, in various stages of development.

*Flowering season.*—Continuously, generally indeterminate, mainly from March to October, depending on light intensity.

*Lastingness of individual blooms.*—Up to 14 days (in a greenhouse in the Spring at 18° C.).

*Fragrance.*—None.

*Peduncle.*—Color: RHS 185A (brownish-purple). Size: Length: 6.0 cm. Diameter: 0.15 cm. Texture: Glabrous, flexible.

Flowers:

*Form of corolla.*—Single-type, 5 petals.

*Shape of corolla.*—Nearly round, with the petals overlapping, almost flat and large.

*Corolla size.*—Length: 8.4 cm. Width: 8.3 cm. Depth: 1.2 cm.

Petals:

*Shape.*—Cordate, weakly lobed at the top end.

*Apex.*—Emarginate.

*Base.*—Attenuate.

*Margin.*—Entire.

*Petal size.*—Top: Length: 3.9 cm. Width: 6.4 cm. Lateral: Length: 4.0 cm. Width: 5.0 cm. Lower: Length: 4.2 cm. Width: 5.2 cm.

*Color.*—General color description: Light violet, fairly uniform, with a small purple eye. Upper surface: RHS N78B, banner petal between RHS N74B and RHS N78. Lower surface: RHS N78B. Eye Zone: Between RHS N74A and RHS N74B (purple), small, almost only at the bases of the lateral petals.

*Petal texture.*—Smooth.

*Aspect.*—Flat.

Spur:

*Shape.*—Downwardly curved.

*Color.*—RHS 53B (dull red).

*Size.*—Length: 5.5 cm to 6.0 cm. Diameter: 0.3 cm (at the flower end).

Reproductive organs:

*Stamens.*—Number: 5 fused. Stamen color (upper surface color): RHS 57B (rose-red) or lighter. Anthers: Fused, hooded. Pollen color: RHS 8D (whitish-yellow).

*Pistils.*—Style and stigma: 5, very short, RHS 150D (pale-yellow). Ovary: 5-celled. Ovary length: 0.5 cm. Ovary color: RHS 143A (surface green).

Fruit and seed set: No seed set observed.

Disease and insect resistance: No particular resistance or susceptibility has been observed.

COMPARISON WITH PARENTAL AND COMMERCIAL CULTIVARS

'Fisnics Thyst' differs from the female parent 'K01-8180-1' (unpatented), by having light-violet flowers and medium green foliage, while 'K01-8180-1' has purple flowers and dark-green foliage.

'Fisnics Thyst' differs from the male parent 'K01-8753-17' (unpatented), by having a more bluish tone of flower color and a somewhat taller and better branched plant habit, while 'K01-8753-17' has purple to violet flowers in combination with medium green foliage and a compact plant habit.

'Fisnics Thyst' differs from the commercial cultivar 'Fisimp 144' (U.S. Plant Pat. No. 13,713) by having wider and rounder flowers of similar color, but with a more distinct eye, somewhat smaller leaves and a somewhat earlier flowering response than 'Fisimp 144'.

'Fisnics Thyst' differs from cultivar 'Fisimp 113' (U.S. Plant Pat. No. 13,695) by having medium green leaves and a somewhat more bluish general flower color than 'Fisimp 113'. Additionally, 'Fisnics Thyst' has a more compact plant habit, while 'Fisimp 113' develops tall plants.

I claim:

1. A new and distinct cultivar of New Guinea *Impatiens* plant as shown and described herein.

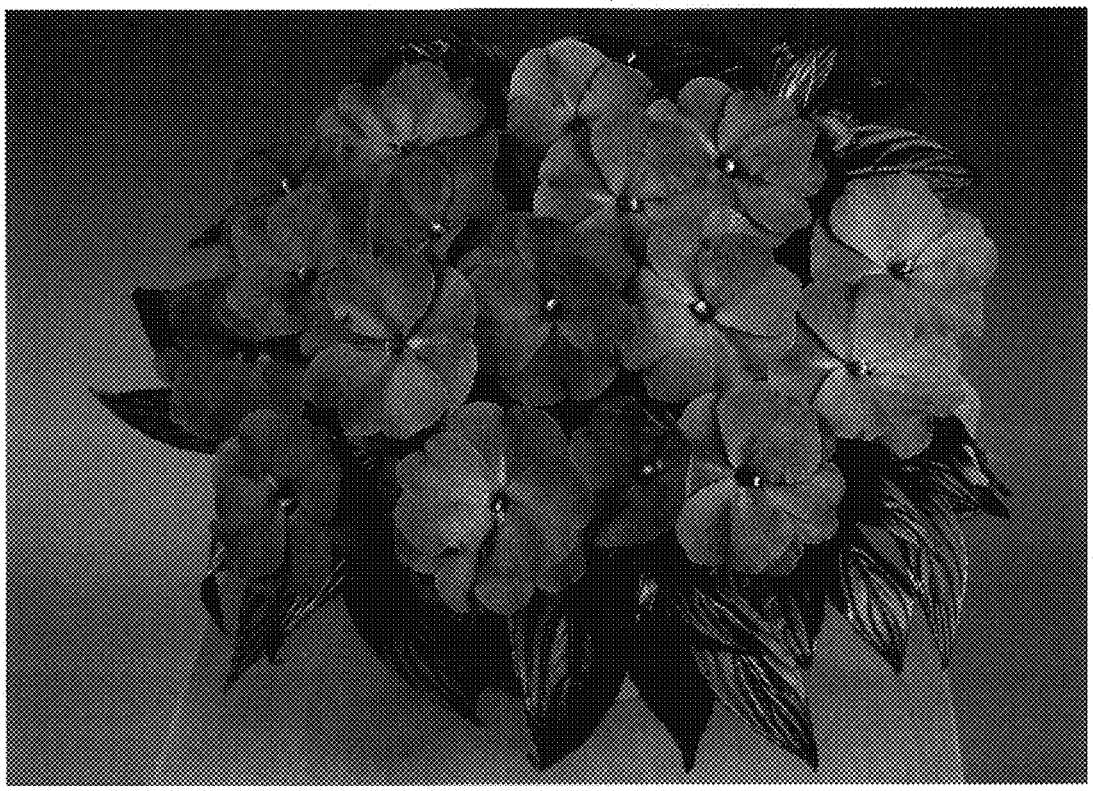

* * * * *